United States Patent
Suzuki

(10) Patent No.: US 7,298,257 B2
(45) Date of Patent: Nov. 20, 2007

(54) TRANSPORTATION DEVICE AND METHOD OF LIVING TISSUES

(75) Inventor: Kei Suzuki, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 319 days.

(21) Appl. No.: 11/208,639

(22) Filed: Aug. 23, 2005

(65) Prior Publication Data

US 2006/0208881 A1 Sep. 21, 2006

(30) Foreign Application Priority Data

Mar. 2, 2005 (JP) ............................. 2005-057734

(51) Int. Cl.
*G08B 1/08* (2006.01)
*G08B 17/00* (2006.01)
*G07B 15/02* (2006.01)
*A61B 19/00* (2006.01)

(52) U.S. Cl. .................... 340/539.12; 340/539.13; 340/572.1; 340/573.1; 340/585; 340/588; 62/371; 700/299; 604/404; 705/2; 702/130; 235/384

(58) Field of Classification Search .......... 340/539.12, 340/572.1, 573.1
See application file for complete search history.

(56) References Cited

U.S. PATENT DOCUMENTS 5,835,012 A * 11/1998 Wilk ..................... 340/539.26

| 7,004,621 | B2 * | 2/2006 | Roberts et al. ............ 374/106 |
| 7,034,689 | B2 * | 4/2006 | Teplitxky et al. ........ 340/572.7 |
| 7,149,658 | B2 * | 12/2006 | Kadaba ..................... 702/184 |
| 7,151,455 | B2 * | 12/2006 | Lindsay et al. .......... 340/572.3 |
| 7,158,028 | B1 * | 1/2007 | Ghahramani ........... 340/539.22 |
| 2004/0212509 | A1 * | 10/2004 | Zweig ........................ 340/588 |
| 2004/0226390 | A1 * | 11/2004 | Beginski .................... 73/865.9 |
| 2006/0006987 | A1 * | 1/2006 | Hashimoto et al. ...... 340/10.51 |
| 2006/0145844 | A1 * | 7/2006 | Chen et al. ............ 340/539.27 |
| 2007/0028642 | A1 * | 2/2007 | Glade et al. .................. 62/371 |

FOREIGN PATENT DOCUMENTS

JP 2004-217290 1/2003

* cited by examiner

*Primary Examiner*—Donnie L. Crosland
(74) *Attorney, Agent, or Firm*—Reed Smith LLP; Stanley P. Fisher, Esq.; Juan Carlos A. Marquez, Esq.

(57) ABSTRACT

A living tissue transportation method includes the steps of: putting the living tissues in a carrying container for transportation (1) having a first memory storing an identifier and an IC tag (10) having a temperature sensor; putting the carrying container (1) in an individual carrying container (2) having a second memory for storing the identifier and a second IC tag (20) having a temperature sensor; storing a copy of the identifier of the IC tag (10) in the memory of the IC tag (20) and putting the individual carrying container (2) in a transportation container for constant temperature (3). A controller (30) provided in the transportation container (3) communicates with the IC tags (10, 20), and writes information indicating a temperature abnormality to the first and second memories when the temperatures of the carrying container (1) and the individual carrying container (2) are out of a predetermined temperature range.

17 Claims, 13 Drawing Sheets

TRANSPORTATION DEVICE AND METHOD OF LIVING TISSUES

CLAIM OF PRIORITY

The present application claims priority from Japanese patent application P2005-57734 filed on Mar. 2, 2005, the content of which is hereby incorporated by reference into this application.

BACKGROUND OF THE INVENTION

This invention relates to a technique of transporting with retaining temperature, and more particularly to a technique of transporting living tissues such as cultured cells.

In transporting medical instruments that contain cell tissues, such as artificially cultured skin or cornea or living tissues taken for inspections, JP 2004-217290 A discloses that transports the medical instruments while keeping the temperature within a predetermined range to avoid damage to the cells (for example, see Patent Document 1). In this technique, medical instruments that contain living tissues are placed in a container having a thermal insulation function and a thermal storage function or having a warming function, and transported with their temperature kept within a predetermined range. A temperature recording device for recording the temperature in the container is provided in order to secure the temperature during the transportation.

SUMMARY OF THE INVENTION

With the related technique, checking, after transportation, to see whether the predetermined temperature range has been kept requires making a judgment by referring to the results recorded by the temperature recording device, which involves labor and time.

Also, with the related technique, if a mistake is made during the process of putting a large number of medical instruments in a single container for transportation, e.g., when a wrong medical instrument is mistakenly put in the container instead of the correct one, the provision of the mistakenly delivered medical instrument cannot be recognized until the container arrives at the destination of delivery and is checked for identification. Particularly, with medical instruments used for a surgical operation of a particular patient, for example, it is necessary to prove that the medical instruments delivered to the destination medical facility are the right products for the patient, but the conventional example just ensures the retainment of temperature of the living tissues and proving the correctness of the delivered products is difficult.

This invention has been made to solve the problems above, and an object of this invention is, in transportation of medical instruments including living tissues, to easily and quickly prove the quality during the transportation and to prove the correctness of the individual medical instruments.

An embodiment of this invention relates to a method of transporting living tissues contained in a container retaining temperature, which includes the steps of: putting the living tissues in a first container including a first storage for storing a predetermined first identifier and a first IC tag including a first temperature sensor for measuring temperature and a radio communication mechanism; putting the first container in a second container including a second storage capable of storing the first identifier of the first IC tag and a second IC tag including a second temperature sensor for measuring temperature and a radio communication mechanism; storing a copy of the first identifier of the first IC tag in the second storage before beginning transportation of the living tissues; putting the second container in a third container having the temperature retaining function; transporting the third container; causing a controller provided in the third container to communicate with the first IC tag and the second IC tag being transported to read the temperatures from the first temperature sensor and the second temperature sensor; and writing information indicating an occurrence of a temperature abnormality to the first storage of the first IC tag and the second storage of the second IC tag when one of the temperatures read from the first temperature sensor and the second temperature sensor is out of a predetermined temperature range.

When the abnormality occurs, an indicator provided in the third container indicates abnormality occurrence information, and when no abnormality occurs, the indicator indicates the temperature of the first temperature sensor or the second temperature sensor.

After the completion of the transportation, the first container and the second container are disposed of together with the first IC tag and the second IC tag.

Thus, according to the embodiment of this invention, before transportation, the identifier of the first IC tag is copied to the second IC tag of the second container for accommodating the first container, and after the transportation, the first identifier copied to the second IC tag is compared with the first identifier read from the first IC tag of the first container, whereby the correctness of the delivered living tissues is proved very easily and quickly.

When a temperature abnormality occurs in the first or second container during the transportation of the living tissues, the indicator indicates the contents of the abnormality. Accordingly, by visually checking the indicator, whether there is an abnormality or not can be known very quickly and easily before the first or second container is taken out from the third container.

Also, because the first and second containers having the first and second IC tags attached thereto are disposed of after use, the containers are kept in a sanitary condition and overwriting of identifiers caused by reuse is avoided, whereby reliabilities are ensured both in sanitation and information (correctness) aspects. Furthermore, because the first and second containers that are disposed of after use are just provided with the first and second IC tags, highly reliable services are offered at suppressed transportation costs.

BRIEF DESCRIPTION OF THE DRAWINGS

The present invention can be appreciated by the description which follows in conjunction with the following figures, wherein.

DETAILED DESCRIPTION OF THE PREFERRED EMBODIMENTS

An embodiment of this invention will now be described referring to the accompanying drawings.

First Embodiment

Figure 1:
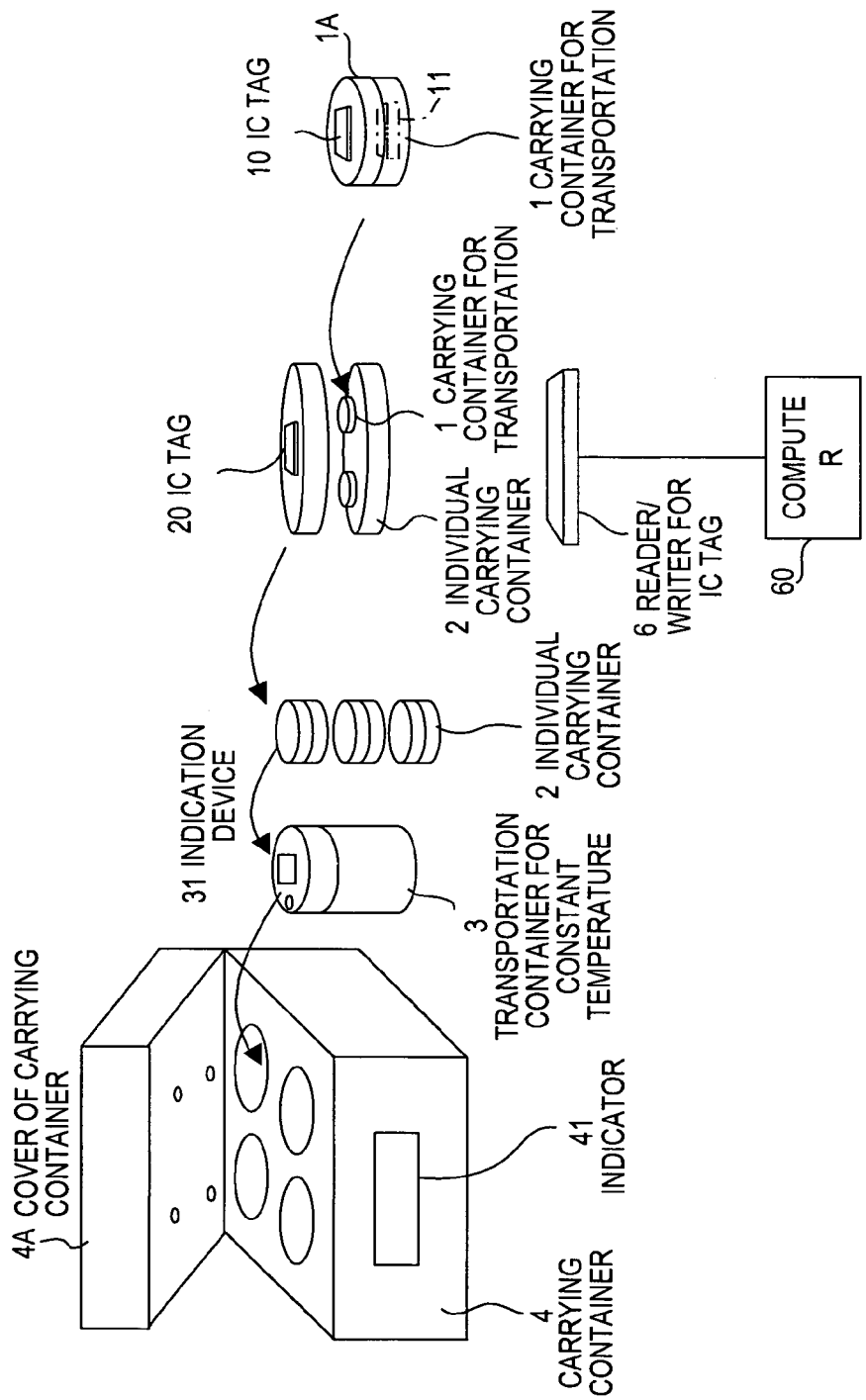
FIG. 1 is an illustrative diagram showing a combination of carrying containers for transportation, individual carrying containers, a transportation container for constant temperature, and a carrying container according to this invention.
Figure 2:
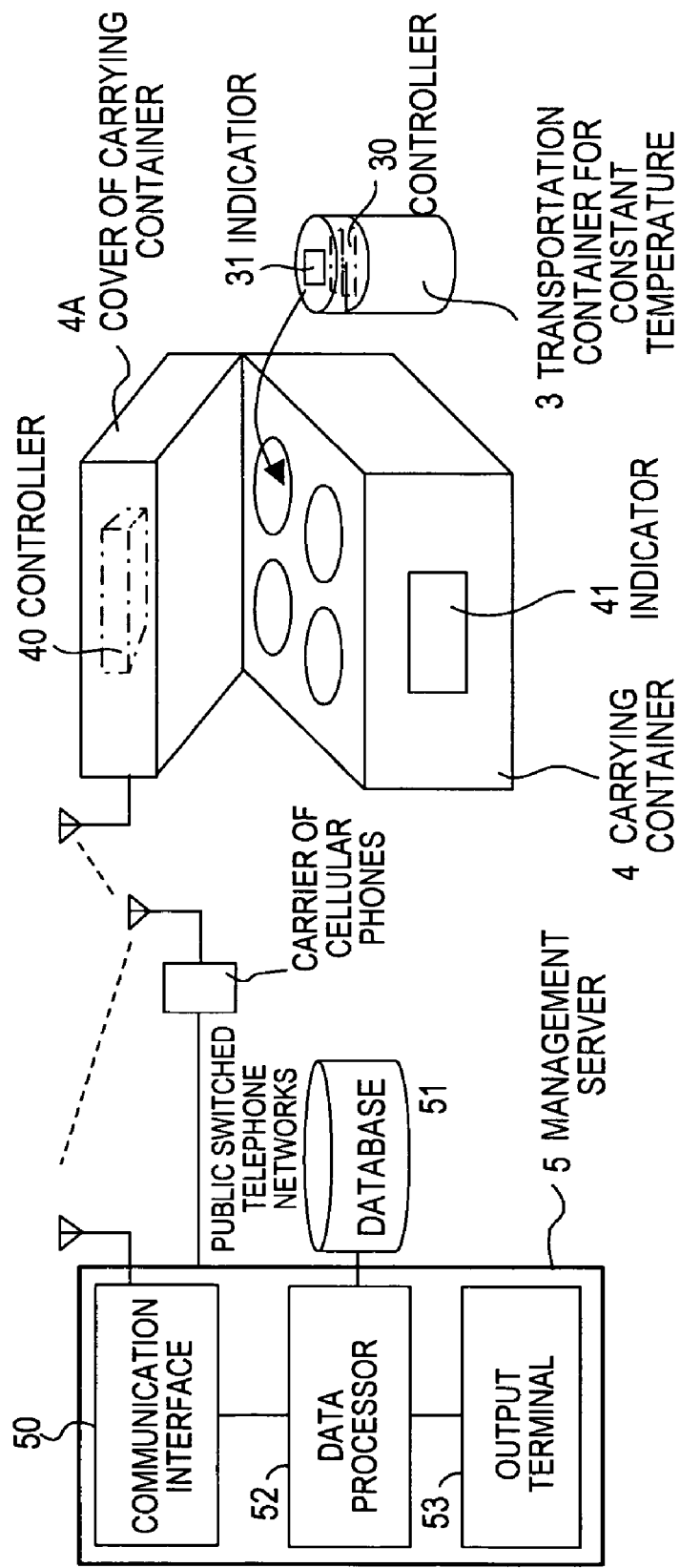
FIG. 2 is a diagram illustrating the outline of the configuration of a transportation system.

FIG. 1 illustrates the structures of containers that are used to accommodate living tissues, such as cultured tissues, according to a first embodiment, and FIG. 2 illustrates the configuration of a transportation system for transporting the living tissues using the containers.

As shown in FIG. 1, a carrying container for transportation (a first container) 1, which is shaped like a laboratory dish, is used to accommodate a medical instrument 11, such as a solution or gel including living tissues like cultured cells or a specimen. A label-like passive IC tag 10 is attached to the cover 1A of the carrying container for transportation 1, where the passive IC tag 10 includes a memory that previously stores a unique identifier (a first identifier) and a temperature sensor for measuring the temperature of the carrying container for transportation 1 (the passive IC tag 10 is hereinafter referred to also as a passive IC tag with temperature sensor, a radio IC tag, or an IC tag). The carrying container for transportation 1 is used as a disposable container that is thrown away without removing the attached IC tag 10 at the destination of delivery after being used for transportation once.

The carrying container for transportation 1 is put in a disk-like individual carrying container 2 (a second container). The individual carrying container 2 is a container for accommodating a plurality of carrying containers for transportation 1. A label-like passive IC tag with temperature sensor 20 with a temperature sensor is attached to the cover 2A of the individual carrying container 2, where the passive IC tag with temperature sensor 20 with a temperature sensor includes a memory that is capable of writing of identifiers (first identifiers) of a plurality of carrying containers for transportation 1 accommodated in the individual carrying container 2. The passive IC tag with temperature sensor 20 with a temperature sensor, attached to the individual carrying container 2, has a previously set unique identifier (a second identifier). The individual carrying container 2 is used as a disposable container that is thrown away without removing the attached IC tag 20 at the destination of delivery after being used for transportation once.

The individual carrying container 2 is made of, e.g., styrene foam having good thermal insulation ability, and it has an internal structure (e.g., recesses) for holding the carrying containers for transportation 1 so as to prevent the carrying containers for transportation 1 from coming off the individual carrying container 2 during transportation.

As will be described later, information is written to and read from the passive IC tag with temperature sensor 20 using a reader/writer for IC tag 6 and a computer 60, where, with the individual carrying container 2 placed on the reader/writer for IC tag 6, identifiers etc. are read from the passive IC tags with temperature sensors 10 of the carrying containers for transportation 1 accommodated in the individual carrying container 2, and are written to the passive IC tag with temperature sensor 20 of the individual carrying container 2.

The individual carrying container 2 is put in a cylindrically-shaped transportation container for constant temperature 3. The transportation container for constant temperature 3 is a cylindrical container for accommodating a plurality of individual carrying containers 2 in a stack, and includes a thermal insulation member and a thermal storage member as described later, so as to retain the temperature of the carrying containers for transportation 1 in the individual carrying containers 2. For example, the thermal insulation member provides thermal insulation from the outside, and the thermal storage member internally keeps the living tissues in the carrying containers for transportation 1 at constant temperature (e.g., around human body temperature).

The transportation container for constant temperature 3 (a third container) has a controller 30 shown in FIG. 2 that reads and writes information to and from the passive IC tags with temperature sensors 10, 20 attached to the carrying containers for transportation 1 and individual carrying containers 2 accommodated inside. Also, an indicator 31 is provided in the cover 3A of the transportation container for constant temperature 3 to indicate conditions of the carrying containers for transportation 1 and presence/absence of abnormalities, for example.

While the transportation container for constant temperature 3 can alone be used for the purpose of transportation this embodiment describes an example which uses a carrying container 4 to hold a plurality of transportation containers for constant temperature 3 in order to transport a larger number of carrying containers for transportation 1.

The carrying container 4 (a fourth container) is shaped like a box in appearance and has cylindrical recesses for holding a plurality of transportation containers for constant temperature 3. The carrying container 4 includes a thermal insulation member to thermally insulate the plurality of individual carrying containers 2 from the outside.

Also, the carrying container 4 has a controller 40 shown in FIG. 2, that sends and receives information to and from the controller 30 of the transportation container for constant temperature 3 placed inside. An indicator 41 is provided in an outer surface 4A of the carrying container 4 to indicate conditions of the carrying containers for transportation 1 kept in the transportation container for constant temperature 3 and presence/absence of abnormalities, for example.

As above, the medical instruments 11 that hold living tissues are accommodated in a nested carrying container 4, transportation containers for constant temperature 3, individual carrying containers 2, and carrying containers for transportation 1, and are transported by vehicle or airplane.

While the carrying container 4 and the transportation containers for constant temperature 3 are repeatedly used, the carrying containers for transportation 1 and the individual carrying containers 2, accommodated inside and having the passive IC tags with temperature sensors 10, 20, are disposed of after being used once. In other words, the containers to which the medical instruments 11, containing solution or gel, or living tissues, may attach because of vibrations during transportation are disposed of after use, in order to keep the containers in a sanitary condition. The passive IC tags with temperature sensors 10 attached to the carrying containers for transportation 1 and the passive IC tags with temperature sensors 20 attached to the individual carrying containers 2 are also used as disposable parts. Because the passive IC tags with temperature sensors 10, 20 store the identifiers of the medical instruments 11 or living tissues, past data on a management server 5 at the control center may be overwritten with different pieces of data if the identifiers are not erased when the passive IC tags with temperature sensors 10, 20 are reused. Accordingly, the carrying containers for transportation 1 and the individual carrying containers 2, with the passive IC tags with temperature sensors 10, 20 having temperature sensors, are disposed of after use, whereby the containers are kept in a sanitary condition and overwriting of identifiers is avoided, thus ensuring reliabilities in both sanitation and information aspects.

FIG. 2 shows the configuration of a transportation system, where the controller 40 (a second controller) of the carrying container 4 has a communication device (a radio communication terminal) to communicate with the management server 5 at the control center through a mobile communication network, such as a cellular phone network or a radio network. The controller 40 of the carrying container 4 also has a position detecting device for detecting the present position by using Global Positioning System (GPS) satellites or the mobile communication network, and the sender of the medical instruments 11 and the medical facility that receives the medical instruments 11 are capable of obtaining information about the conditions and present position of the medical instruments 11 being transported, by making inquiries to the management server 5.

For this purpose, the management server 5 includes a communication interface 50 connected to the mobile communication network, a database 51 for storing information obtained from the passive IC tags with temperature sensors 10, 20 attached to the carrying containers for transportation 1 and the individual carrying containers 2, a data processor 52 for controlling access to the database 51, and an output terminal 53 including a display device. The output terminal 53 is provided for use by operators etc. in the control center. The communication interface 50 is connected also to a wired network to allow communication with the sender and medical facility.

Figure 3:
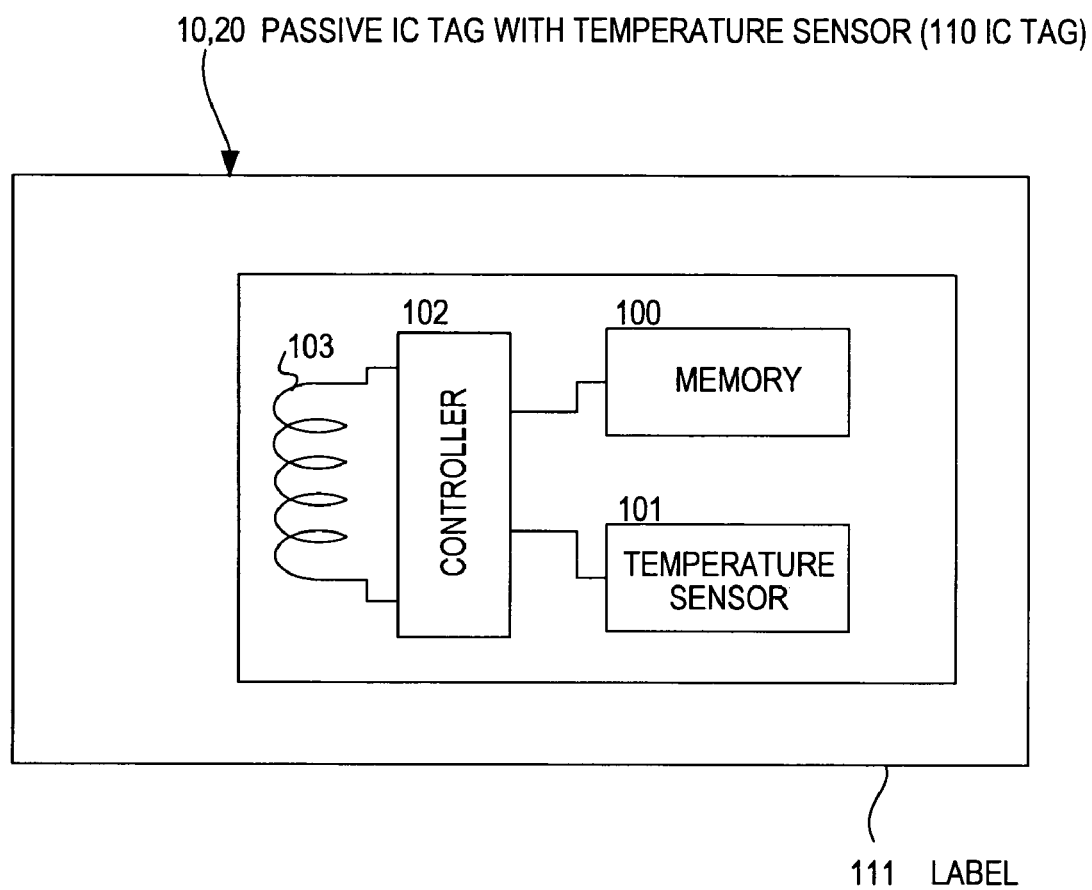
FIG. 3 is a block diagram illustrating the configuration of a passive IC tag with a temperature sensor.

FIG. 3 is a block diagram illustrating the configuration of the passive IC tags with temperature sensors 10, 20 with temperature sensors. Because the passive IC tags with temperature sensors 10 attached to the carrying containers for transportation 1 and the passive IC tags with temperature sensors 20 attached to the individual carrying containers 2 have same configuration, the description below shows only a passive IC tag with a temperature sensor 10.

As shown in FIG. 3, the passive IC tag with a temperature sensor 10 (radio IC tag 110), having a temperature sensor 101 and a memory for storing information including an identifier, is attached to a label (or a sticker) 111, which can be bonded on the surface of the carrying container for transportation 1.

The radio IC tag 110 includes a controller 102 that writes and reads information to and from the memory 100 and reads measured temperature from the temperature sensor 101, and an antenna 103 for communication with the controllers 30 and 40 of the transportation container for constant temperature 3 and carrying container 4. The controller 102 has a radio communication module. When receiving a given signal from the controller 30, the controller 102 writes and reads information to and from the memory 100, or reads data from the temperature sensor 101 and sends the data to the controller 30, or writes information from the controller 30 to the memory 100. For example, the memory 100 is formed of a flash memory capable of holding stored information without power supply. For example, the radio IC tag 110 is configured as described in JP 2004-348469 A.

The surface of the label 111 has an area where information about the contents can be printed or written by hand.

A unique identifiers is previously set for the passive IC tag with a temperature sensor 10 (radio IC tag 110). For example, the label-like passive IC tag with temperature sensor 10 is attached when a medical instrument 11 or living tissues are put in the carrying container for transportation 1, and the unique identifier is written in the memory 100 with the reader/writer for IC tag 6 shown in FIG. 1, for example.

As for the passive IC tag with temperature sensor 20 attached to the individual carrying container 2, a unique identifiers is written in after carrying containers for transportation 1 have been put therein, as will be described later.

Information written to the label-like passive IC tag with temperature sensor 10 attached to the carrying container for transportation 1 may include additional information as shown below, in addition to the identifiers. The example below assumes transportation of cultured tissues as living tissues.

(1-1-1) Identification number of a product, e.g., order number of the cultured tissues (1-1-2) Name (or identification code) of the hospital as the destination of delivery (1-1-3) Shipping date and time (1-1-4) Due time of arrival (1-1-5) Name (or identification code of, e.g., medical record) of the patient who uses the cultured tissues (1-1-6) Information for identifying the patient (birthday, password, or biometrics information such as fingerprints)

(1-1-7) Name of part of the cultured tissues (1-1-8) Shipper name (1-1-9) Abnormality information (initial value is "normal"), (kind of abnormality, time of occurrence)

(1-1-10) Kind of container ("carrying container", "individual carrying container")

Information written to the passive IC tag with temperature sensor 20 attached to the individual carrying container 2 may include additional information as shown below, as well as the above-described identifiers.

(1-2-1) Identification number of a product, e.g. order number of the cultured tissues (1-2-2) Name (or identification code) of the hospital as the destination of delivery (1-2-3) Shipping date and time (1-2-4) Due time of arrival (1-2-5) Name (or identification code of, e.g., medical record) of the patient who uses the cultured tissues (1-2-6) identifier(s) of tags attached to all "carrying containers" accommodated therein (1-2-7) Shipper name (1-2-8) Abnormality information (initial value is "normal"), (kind of abnormality, time of occurrence)

(1-2-10) Kind of container ("carrying container", "individual carrying container")

Figure 4:
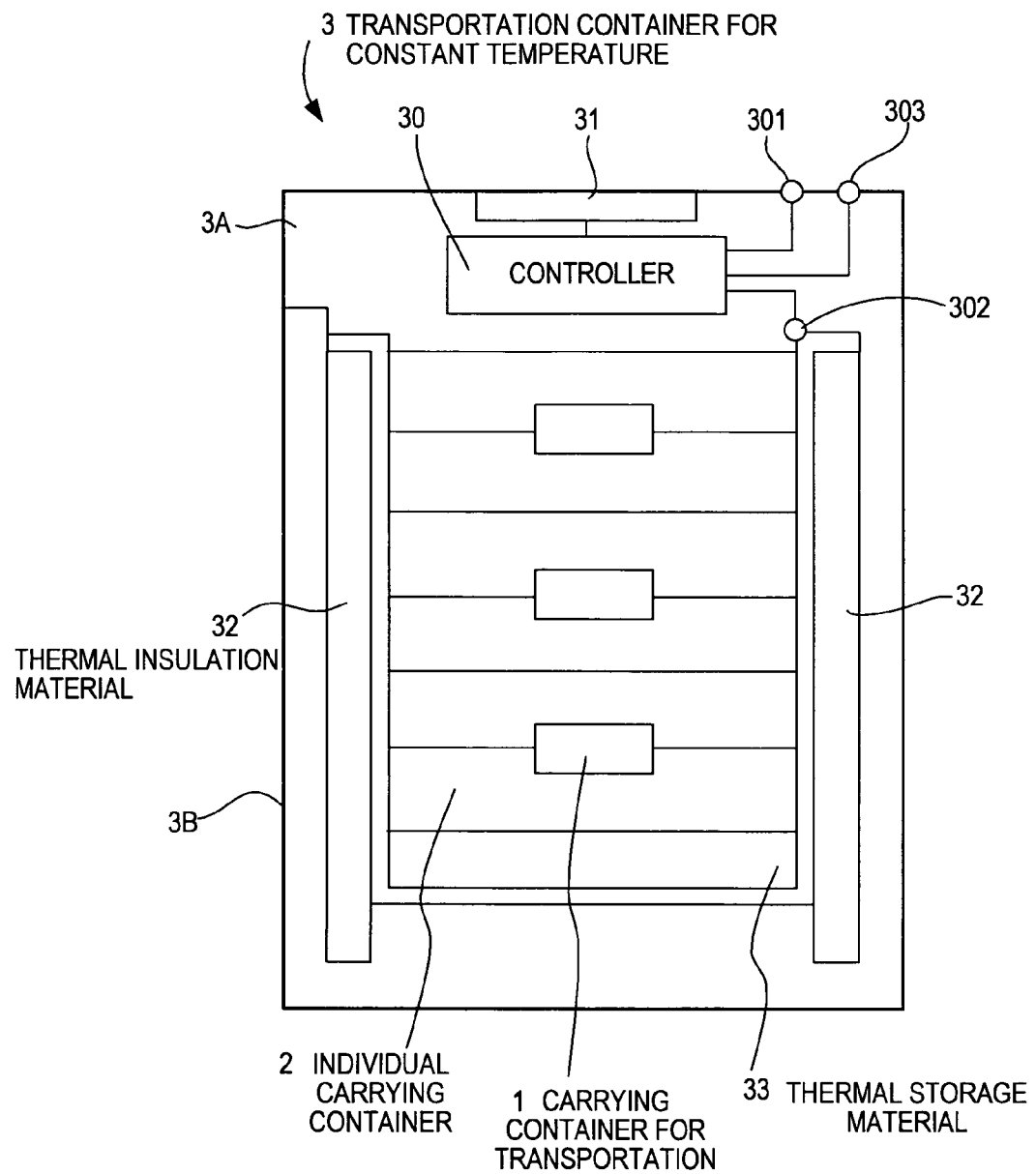
FIG. 4 is a cross-sectional view of the constant-temperature transportation container.

Next, FIG. 4 illustrates the structure of the transportation container for constant temperature 3 that accommodates a plurality of individual carrying containers 2 and is accommodated in the carrying container 4.

The cylindrically-shaped transportation container for constant temperature 3 mainly includes a container body 3B having an inside space for accommodating a stack of a plurality of (in this example, three) disk-like individual carrying containers 2, and the cover 3A formed to be capable of opening and closing at the top of the container body 3B.

The container body 3B includes a thermal insulation material 32 placed to surround the space accommodating individual carrying containers 2A, and a thermal storage material 33 placed at the bottom of the space to keep the temperature of the individual carrying containers 2 and carrying containers for transportation 1 in the individual carrying containers 2.

Figure 5:
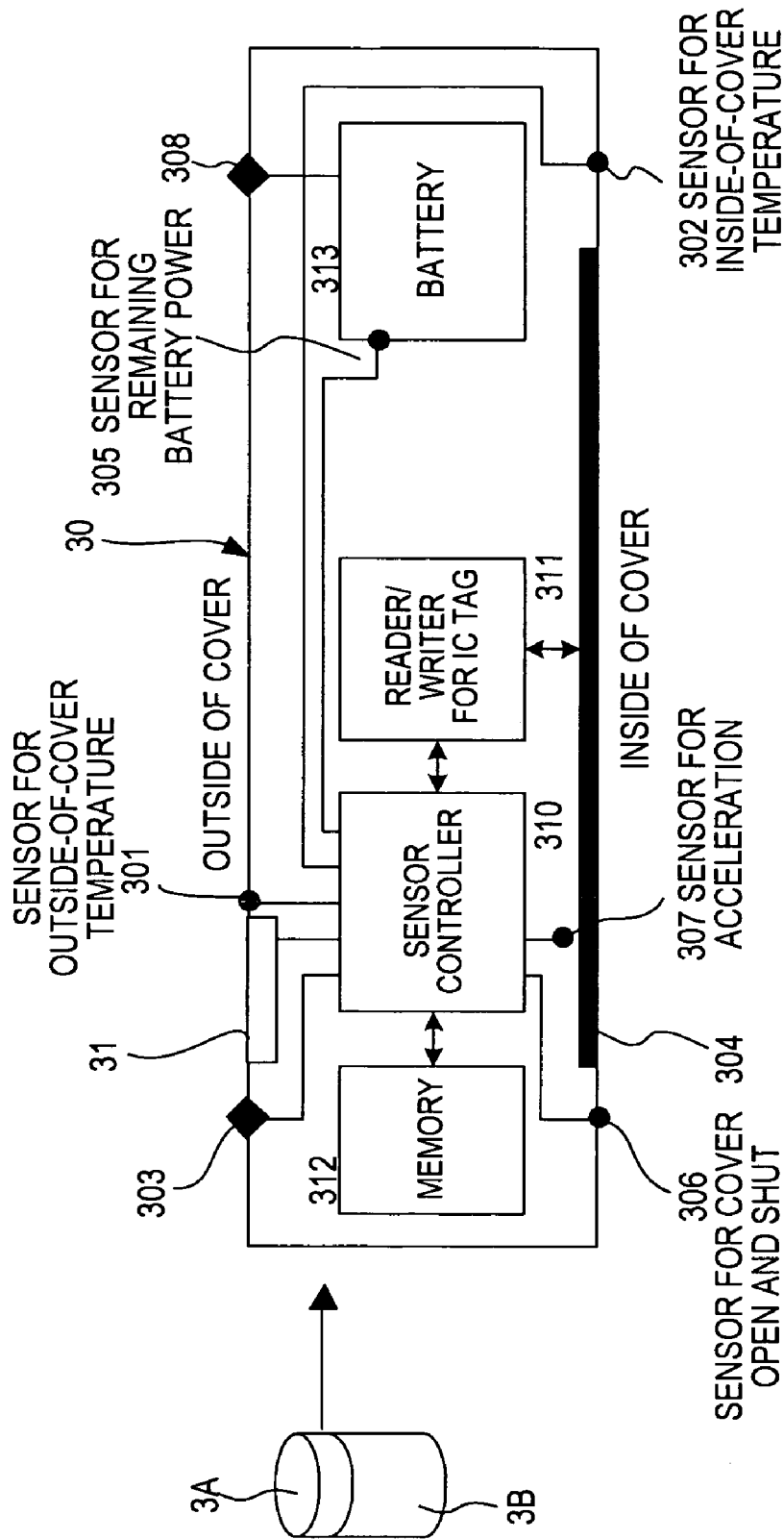
FIG. 5 is a block diagram of a controller of the constant-temperature transportation container.

The opening/closing cover 3A is provided at the top of the transportation container for constant temperature 3. The controller 30 shown in FIG. 5 is provided in the cover 3A.

The indicator 31 is placed in the top surface of the cover 3A. The indicator 31 is connected to the controller 30 and indicates conditions of the inside temperature and presence/absence of abnormalities. Also provided in the top surface of the cover 3A are an output terminal for external data 303 for communication with the carrying container 4, an sensor for outside-of-cover temperature 301 for detecting the temperature outside of the transportation container for constant temperature 3, and a terminal for battery charging 308, for charging a battery as will be described later.

Disposed on the inner side of the cover 3A are an sensor for inside-of-cover temperature 302 for sensing the temperature inside the transportation container for constant temperature 3, an antenna 304 for a reader/writer 311 for communicating with the passive IC tags with temperature sensors 10, 20 of the individual carrying containers 2 and carrying containers for transportation 1, and a sensor for cover open and shut 306, for sensing opened state of the cover 3A. Further, the controller 30 includes a sensor for acceleration 307 for sensing the acceleration applied to the transportation container for constant temperature 3, and a sensor for remaining battery power 305, for sensing the amount of charge of a battery 313.

Also, though not shown, a switch is provided in a given position on the cover 3A to start/stop the controller 30.

Next, the controller 30 of the transportation container for constant temperature 3 will be described referring to FIG. 5. The cover 3A includes therein the controller 30 which is mainly composed of a sensor controller 310 that plays the major role in the control of the transportation container for constant temperature 3, the reader/writer 311 for communicating with the accommodated passive IC tags with temperature sensors 10, 20 through the antenna 304, a memory 312 for storing collected information and the like, and the battery (rechargeable battery) 313 for supplying power to individual circuits.

The sensor controller 310 collects information from the sensors, terminals, and the reader/writer 311 periodically (e.g. with predetermined cycles) and stores the collected information in the memory 312.

Also, as will be described later, the sensor controller 310 checks the information collected from the sensors to judge whether or not there are abnormalities. When an abnormality is detected, the reader/writer 311 writes the kind of the abnormality and the time of occurrence to the passive IC tags with temperature sensors 10, 20. Such abnormalities include deviations from predetermined ranges of the temperature inside the transportation container for constant temperature 3 and the temperatures sensed by the passive IC tags with temperature sensors 10, 20, detection of acceleration over a predetermined reference value (detection of impact), and opening of the cover 3A during transportation.

Figure 6:
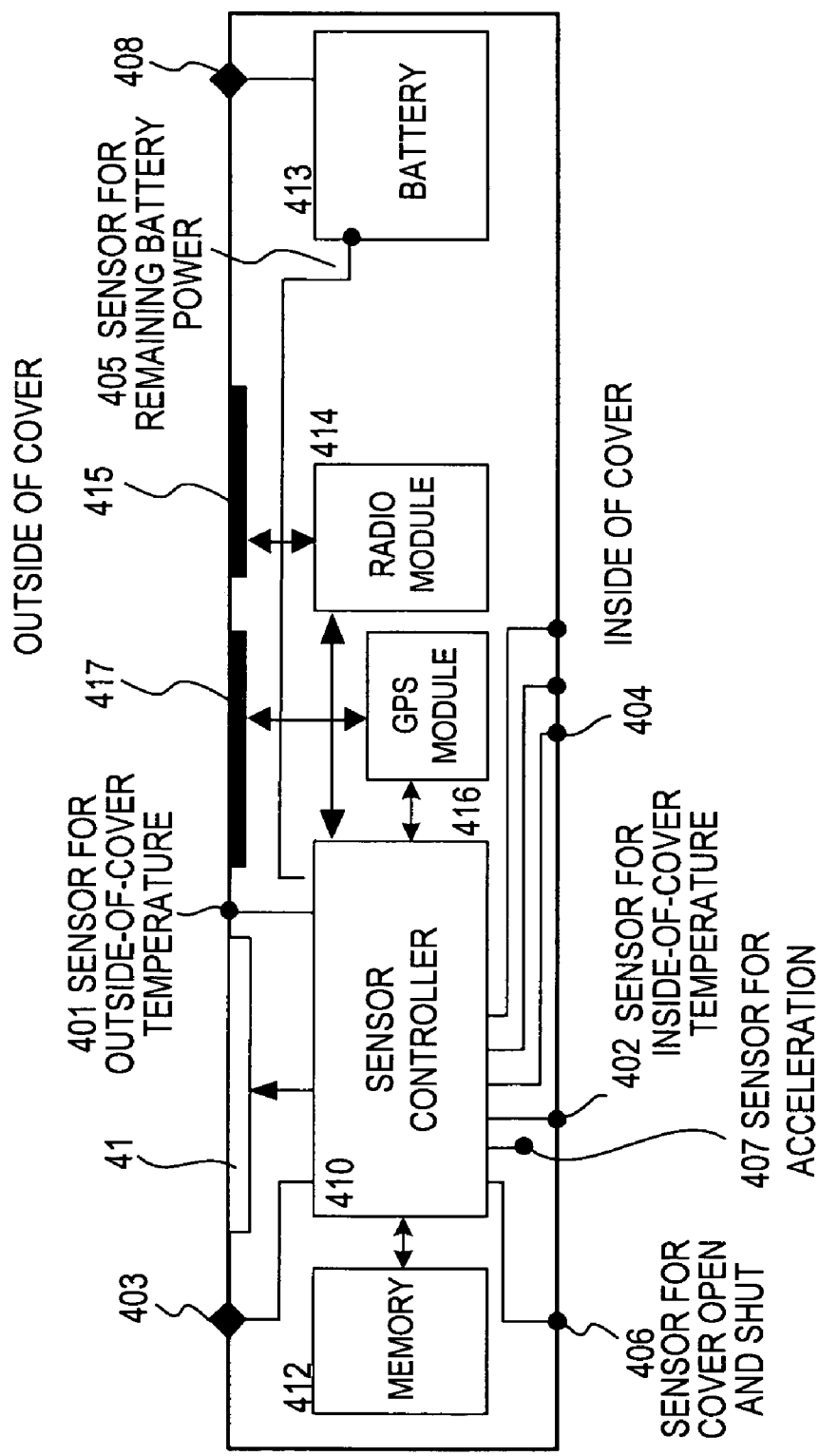
FIG. 6 is a block diagram of a controller of the carrying container.

Next, as shown in FIG. 6, the cover 4A of the carrying container 4 includes the controller 40 for managing a plurality of transportation containers for constant temperature 3 accommodated therein.

The cover 4A is provided, which can open and close at the top of the carrying container 4. The cover 4A includes the controller 40 inside.

The indicator 41 is disposed in the top surface of the cover 4A and is connected to the controller 40 to indicate conditions including the inside temperature and presence/absence of abnormalities. Also provided in the top surface of the cover 4A are an output terminal for external data 403 for communication with an external computer, which is not shown, an sensor for outside-of-cover temperature 401 for detecting the temperature outside of the carrying container 4, and a terminal for battery charging 408, for charging a battery 413. Also, placed in the top surface of the cover 4A are a radio terminal antenna 415 for communicating with the mobile communication network shown in FIG. 2, and an antenna for GPS 417 for receiving information from GPS satellites to detect the present position.

Disposed on the inner side of the cover 4A are an sensor for inside-of-cover temperature 402 for sensing the temperature inside the carrying container 4, connection terminals 404 for communication with the controllers 30 of transportation containers for constant temperature 3 accommodated inside, and a sensor for cover open and shut 406, for sensing opening of the cover 4A. Further, the controller 40 includes a sensor for acceleration 407 for sensing the acceleration applied to the carrying container 4, and a sensor for remaining battery power 405, for sensing the amount of charge of the battery 413. The connection terminals 404 are in contact with the output terminals for external data 303 of the transportation containers for constant temperature 3 accommodated inside.

Also, though not shown, a switch is provided in a given position on the cover 4A to start/stop the controller 40.

Next, the controller 40 of the carrying container 4 includes a sensor controller 410 for communication with the accommodated transportation containers for constant temperature 3 through the connection terminals 404 and for external communication to collect and transfer information, a memory 412 for storing collected information etc., a radio module 414 for communication with the mobile communication network through the radio communication antenna 415, a GPS module 416 for measuring the present position of the carrying container 4 from information received at the antenna for GPS 417, and the battery (rechargeable battery) 413 for supplying power to the individual circuits.

The sensor controller 410 collects information from the sensors and connection terminals 404 with predetermined cycles and stores the collected information in the memory 412.

Also, as will be described later, the sensor controller 410 checks information collected from the sensors to judge whether or not there are abnormalities. When an abnormality has been detected, the sensor controller 410 instructs the controller 30 of the transportation container for constant temperature 3 through the connection terminal 404 to write the kind of the abnormality and the time of occurrence to the passive IC tags with temperature sensors 10, 20 being transported.

Figure 7:
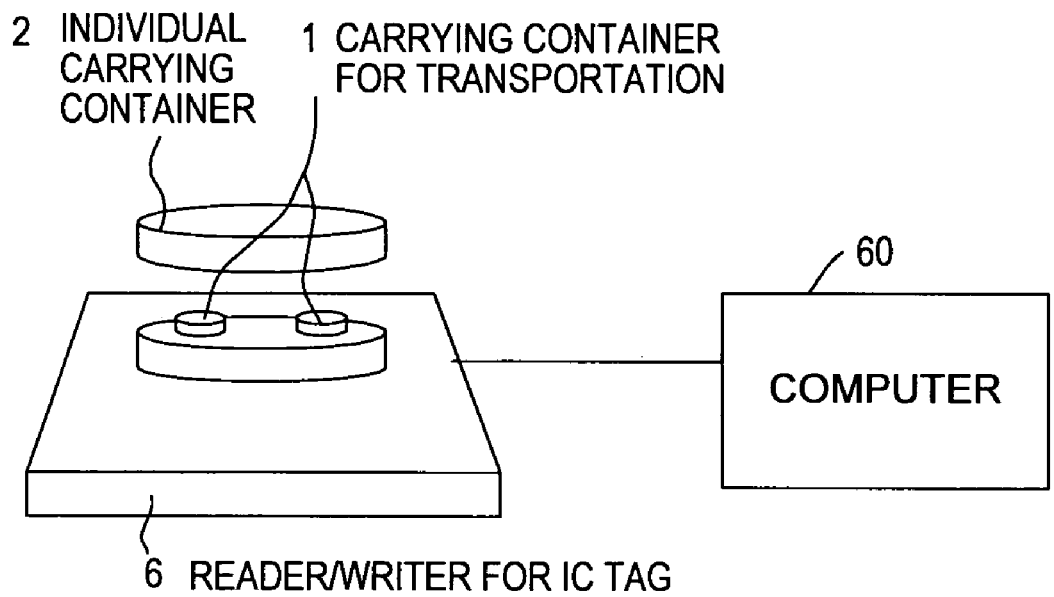
FIG. 7 is an illustrative diagram showing how a reader/writer reads and writes information from and to passive IC tags attached to the carrying containers for transportation and individual carrying container.
Figure 8:
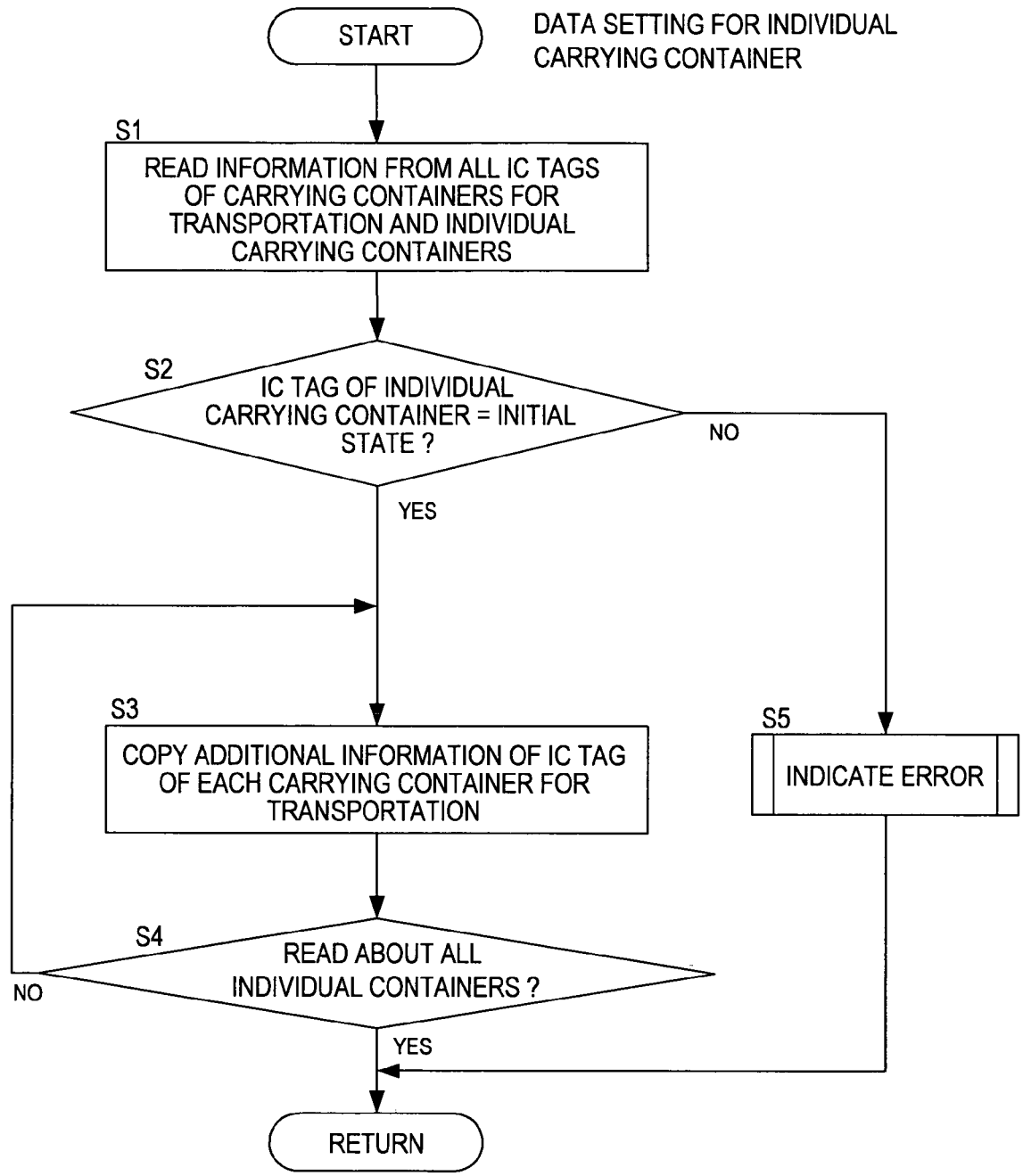
FIG. 8 is a flowchart showing a process in which the reader/writer writes information to the passive IC tag attached to the individual carrying container.

Next, FIG. 7 and FIG. 8 illustrate a preparation for transportation of medical instruments that contain cultured living tissues by using the carrying containers for transportation 1, individual carrying containers 2, transportation container for constant temperature 3, and carrying container 4. FIG. 7 is an illustrative diagram used to describe the process of writing information about the carrying containers for transportation 1 to the passive IC tag with temperature sensor 20 of the individual carrying container 2, and FIG. 8 is a flowchart showing the process of writing information about the carrying containers for transportation 1 to the passive IC tag with temperature sensor 20 of the individual carrying container 2.

First, each carrying container for transportation 1, accommodating a medical instrument including living tissues, is provided with a passive IC tag (IC tag) 10 in which information about the accommodated cultured tissues is previously written. Then, the carrying containers for transportation 1 to be transported are put in the individual carrying container 2.

While an IC tag 20 is attached to the individual carrying container 2, the IC tag 20 contains information indicating an initial state.

Then, as shown in FIG. 7, for shipment, the individual carrying container 2, containing a required number of carrying containers for transportation 1, is placed on the reader/writer for IC tag 6 connected to the computer 60, and the computer 60 performs the processing shown in FIG. 8.

In step S1 of FIG. 8, information is read from all IC tags 10 and 20, which are denoted as IC tags in the diagram placed on the reader/writer for IC tag 6. Now, with the IC tags 10 and 20 on the reader/writer for IC tag 6, all IC tags 10 attached to the carrying containers for transportation 1 should contain the same additional information, and the IC tag 20 of the individual carrying container 2 should be in an initial state, and thus only one of the IC tags contains nothing (an initial state).

In step S2, a check is made to confirm that one of the read values indicates an initial state and all remaining values indicate the same additional information as mentioned above. When the check does not show that only the IC tag 20 of the individual carrying container 2 indicates initial information, then the process goes to step S5 to cause the display device of the computer 60 to show a message indicating an abnormality and error information.

When the values read from the IC tags 10 and 20 indicate the expected condition (i.e., when additional information from one IC tag indicates an initial state and the remaining IC tags indicate the same additional information), the process goes to step S3 and step S4 to write the information about all IC tags 10 attached to the carrying containers for transportation 1 to the IC tag 20 attached to the individual carrying container 2. In this process, the copying operations are performed as below.

(1-1-1) Identification number of the cultured tissues→(1-2-1) Identification number of the cultured tissues (1-1-2) Name (or identification code) of the hospital as the destination of delivery→(1-2-2) Name (or identification code) of the hospital as the destination of delivery (1-1-3) Shipping date and time→(1-2-3) Shipping date and time (1-1-4) Due time of arrival→(1-2-4) Due time of arrival (1-1-5) Name (or identification code of, e.g., medical record) of the patient who uses the cultured tissues→(1-2-5)

(1-1-8) Shipper name→(1-2-7) Shipper name

Further, the identifier information about all IC tags 10 attached to the carrying containers for transportation 1 is stored in the area 1-2-6) of the IC tag 20 of the individual carrying container 2 and "individual carrying container" information is stored in the area (1-2-10).

In this way, the reader/writer for IC tag 6 copies the information from the IC tags 10 of the accommodated carrying containers for transportation 1 to the IC tag 20 of the individual carrying container 2 that is in the initial state.

After that, as shown in FIG. 1, a plurality of individual carrying containers 2 are put in a transportation container for constant temperature 3 and the cover 3A is closed, and then the controller 30 of the transportation container for constant temperature 3 is started. Then, the transportation container for constant temperature 3 is put in the carrying container 4, the cover 4A is closed, and the controller 40 is started.

Next, operations performed by the controller 30 of the transportation container for constant temperature 3 will be described referring to the flowchart of FIG. 9.

After the controller 30 is turned "ON", all flags set in the memory 312 are turned "OFF", and the sensor for acceleration 307 continuously operates to monitor the acceleration. Then, according to the flowchart of FIG. 9, the sensors are driven periodically (e.g., once in every five minutes) using an interval timer, which is not shown in the sensor controller 310, and the sensor controller 310 reads the measurements from the sensors. The sensor values are then checked for abnormalities. As for the value measured by the sensor for acceleration 307 and the value detected by the sensor for cover open and shut 306, the sensor controller 310 stores the values in the memory 312 only for a predetermined time period (e.g., five minutes).

First, in step S10, the reader/writer for IC tag 311 reads the identifiers from the IC tags 20 of the individual carrying containers 2 placed in the transportation container for constant temperature 3 and the IC tags 10 of the carrying containers for transportation 1 in the individual carrying containers 2. Then, in step S11 and step S12, the measured values of the temperature sensors 101 are read from the IC tags 10 and 20 of the individual carrying containers 2 and the carrying containers for transportation 1.

In step S13, the value measured by the sensor for outside-of-cover temperature 301 attached to the cover 3A of the transportation container for constant temperature 3 is read.

In step S14, the value measured by the sensor for inside-of-cover temperature 302 attached to the cover 3A of the transportation container for constant temperature 3 is read.

In step S15, the value measured by the sensor for remaining battery power 305 of the transportation container for constant temperature 3 is read. In step S16, the value of the sensor for acceleration 307 of the transportation container for constant temperature 3 is read from the memory 312. Similarly, in step S17, the value of the sensor for cover open and shut 306 of the transportation container for constant temperature 3 is read from the memory 312.

Next, in step S18, the read acceleration value is compared with a predetermined acceleration range. When the measured value is out of the predetermined acceleration range, it is judged that an abnormality, an application of great impact, has occurred and goes to step S19. On the other hand, when the measured acceleration value is within the predetermined acceleration range, it is judged that the acceleration is normal and goes to step S20.

When it is detected that an acceleration becomes out of predetermined acceleration range, in step S19, an "impact flag" is turned "ON" in the memory 312 and the time when the out of the acceleration range is detected is recorded. When the flag is already ON, the first abnormality is recorded without making a new record.

Next, in step S20, the temperature values read from the individual carrying containers 2 and the carrying containers for transportation 1 are compared with a predetermined temperature range. When the measured values are out of the predetermined temperature range, it is judged that an abnormality in retaining the temperature has occurred and goes to step S21. On the other hand, when the measured temperature values are within the predetermined temperature range, it is judged that the temperatures of the individual carrying containers 2 and carrying containers for transportation 1 are normal and goes to step S22.

When an abnormality has occurred in any of the individual carrying containers 2 and carrying containers for transportation 1, in step S21, an "internal container temperature abnormality flag" in the memory 312 is turned "ON" and the time (present time) is recorded. When the flag is already ON, the first abnormality is recorded without making a new record. An internal temperature abnormality flag is set for each of the accommodated carrying containers for transportation 1 and individual carrying containers 2, and the temperature and time are recorded for each identifier.

Next, in step S22, the temperature value read from the sensor for outside-of-cover temperature 301 is compared with a predetermined temperature range. When the measured value is out of the predetermined temperature range, it is judged that an abnormality of outside temperature has occurred and goes to step S23. On the other hand, when the measured temperature value is within the predetermined temperature range, it is judged that the temperature outside of the cover 3A is normal and goes to step S24.

When it is detected that the temperature outside of the cover 3A becomes out of predetermined temperature range, in step S23, an "outside temperature abnormality flag" in the memory 312 is turned "ON" and the time when the out of the temperature range is detected is recorded. When the flag is already ON, the first abnormality is recorded without making a new record.

Next, in step S24, the remaining battery power (voltage) read from the sensor for remaining battery power 305 is compared with a predetermined voltage value. When the measured value is below the predetermined voltage value, it is judged that an abnormality of remaining battery power has occurred and goes to step S25. On the other hand, when the measured voltage value is over the predetermined voltage, it is judged that the remaining battery power of the battery 313 is normal and goes to step S26.

When it is detected that the remaining battery power becomes predetermined low level, in step S25, a "remaining battery power abnormality flag" in the memory 312 is turned "ON" and the time when the low battery power is detected is recorded. When the flag is already ON, the first abnormality is recorded without making a new record.

Next, in step S26, the temperature value read from the sensor for inside-of-cover temperature 302 is compared with a predetermined temperature range. When the measured value is out of the predetermined temperature range, it is judged that an abnormality of inside-of-cover temperature has occurred and goes to step S27. On the other hand, when the measured inside-of-cover temperature value is within the predetermined temperature range, it is judged that the temperature inside the cover 3A is normal and goes to step S28.

When it is detected that the temperature inside the cover 3A becomes out of predetermined temperature range, in step S27, an "inside temperature abnormality flag" in the memory 312 is turned "ON" and the time when the out of the temperature range is detected is recorded. When the flag is already ON, the first abnormality is recorded without making a new record.

Next, in step S28, a comparison is made to see whether or not the detected value read from the sensor for cover open and shut 306 attained a value indicating "open" (e.g., ON). When the detected value indicates "open", it is judged that an abnormality has occurred, i.e., the cover 3A opened during the transportation, and goes to step S29. On the other hand, when the detected value from the sensor for cover open and shut 306 indicates "close" (e.g., OFF), it is judged that the cover 3A is in the normal condition and goes to step S30.

When it is detected that the cover 3A opened, in step S29, a "cover-open flag" in the memory 312 is turned "ON" and the time when the opening of the cover is detected is recorded. When the flag is already ON, the first abnormality is recorded without making a new record.

In the above-described abnormality information recording steps S19, S21, S23, S25, S27, and S29, the indicator 31 indicates occurrence of abnormality when even one of the abnormality flags is ON.

Then, in step S30, when even one of the abnormality flags is ON, and the currently written abnormality information indicates "normal" or abnormality of lower-priority kind, the reader/writer for IC tag 311 writes the kind of higher-priority abnormality information and the present time to all IC tags 10 and 20 in the transportation container for constant temperature 3. Also, when abnormality information is recorded in the abnormality flags, the data is sent to the controller 40 of the carrying container 4 through the output terminal for external data 303.

On the other hand, when all abnormality flags are OFF, the indicator 31 indicates the present temperature of the carrying containers for transportation 1 or individual carrying containers 2.

Now, the priorities of the abnormality information are set in order of: internal container temperature abnormality>inside temperature abnormality>impact>cover-open state>outside temperature abnormality>remaining battery power abnormality.

The controller 30 writes abnormality information to the IC tags 10 and 20 in the four kinds of recording modes shown below. They are previously set for each transportation container for constant temperature 3 (a switch may be provided to select the recording modes).

(D-1) No record mode: Nothing is recorded.

(D-2) All record mode: All sensor information is recorded. However, because the measured value of the sensor for acceleration 307 is obtained continuously, recording the whole information results in a huge amount of data, and so the acceleration is recorded only when an abnormality occurs.

(D-3) At-the-time-of-abnormality record mode: A record is made only when conditions are met in the abnormality judgements of steps S18 to S28.

Figure 9:
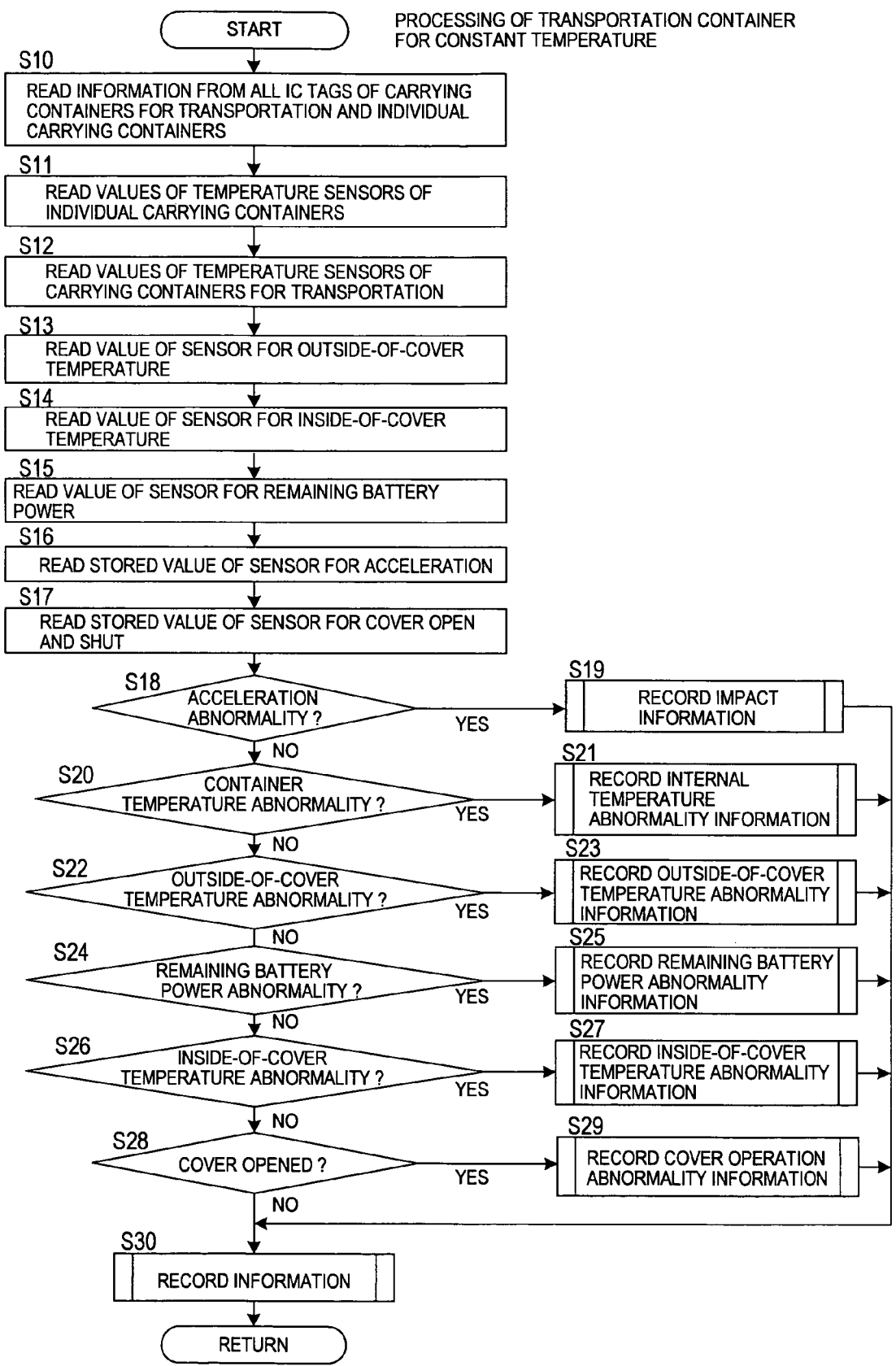
FIG. 9 is a flowchart showing a process performed by the controller of the constant-temperature transportation container.

As above, during transportation of the transportation container for constant temperature 3, the controller 30 performs the operations shown in FIG. 9 to monitor the conditions of the contents of the transportation container for constant temperature 3 (individual carrying containers 2, and carrying containers for transportation 1).

Next, operations performed by the controller 40 of the carrying container 4 will be described referring to the flowchart of FIG. 10.

After the controller 40 is turned "ON", all flags set in the memory 412 are turned "OFF", and the sensor for acceleration 407 continuously operates to monitor the acceleration. Then, according to the flowchart of FIG. 9, the sensors are driven periodically (e.g., once in every five minutes) using an interval timer, which is not shown in the sensor controller 410, and the sensor controller 410 reads the measurements from the sensors. The sensor values are then checked for abnormalities. As for the value measured by the sensor for acceleration 407 and the value detected by the sensor for cover open and shut 406, the sensor controller 410 stores the values in the memory 412 only for a predetermined time period (e.g., for five minutes).

Figure 10:
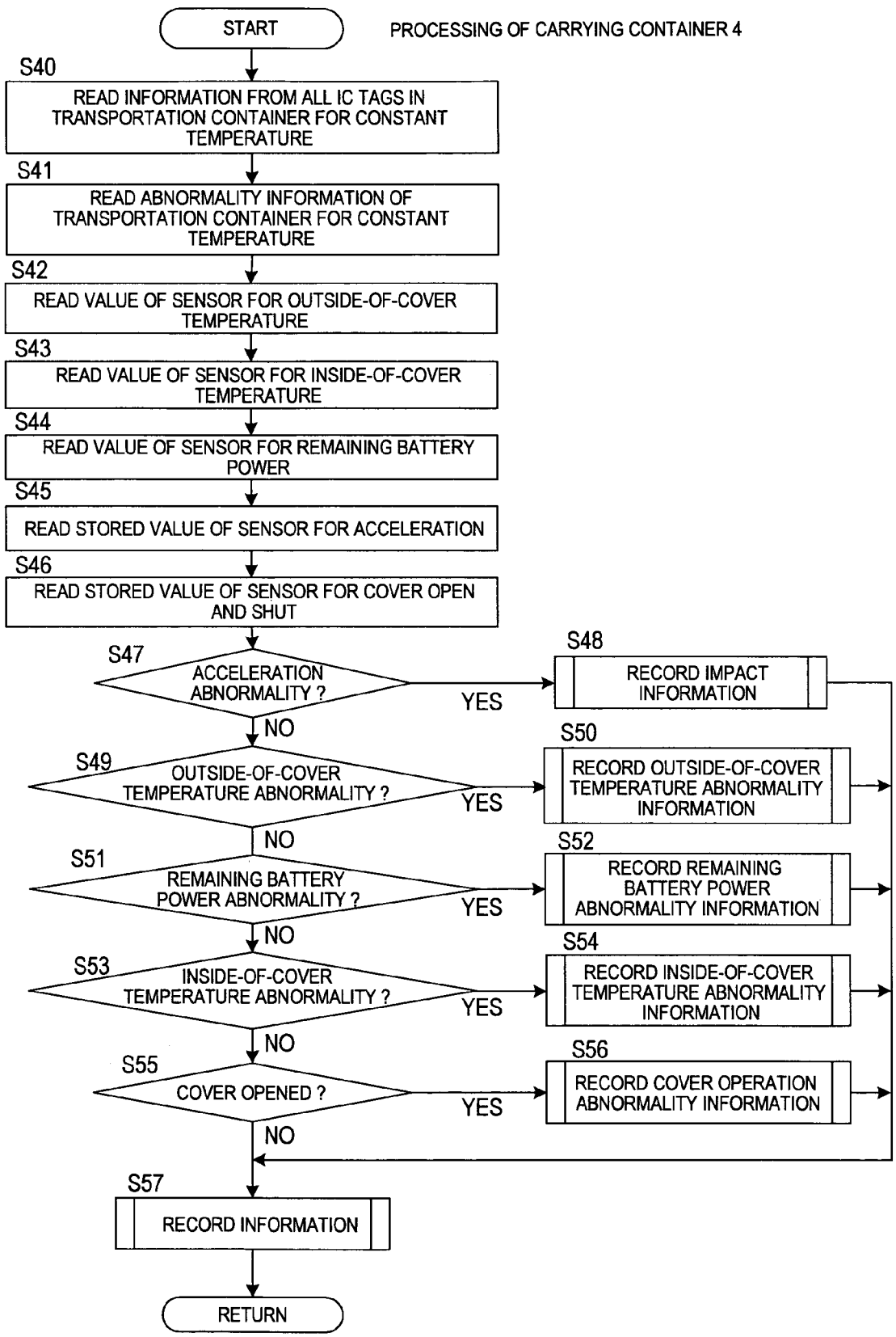
FIG. 10 is a flowchart showing a process performed by the controller of the carrying container.

In FIG. 10, the identifiers of all IC tags 10 and 20 are read in step S40 from the transportation container for constant temperature 3 accommodated in the carrying container 4 through the connection terminal 404, and the abnormality information on the controller 30 is read in step S41.

In step S42, the value measured by the sensor for outside-of-cover temperature 401 attached to the cover 4A of the carrying container 4 is read.

In step S43, the value measured by the sensor for inside-of-cover temperature 402 attached to the cover 4A of the carrying container 4 is read.

In step S44, the value measured by the sensor for remaining battery power 405 of the carrying container 4 is read. In step S45, the value of the sensor for acceleration 407 of the carrying container 4 is read from the memory 412. Similarly, in step S46, the value of the sensor for cover open and shut 406 of the carrying container 4 is read from the memory 412.

Next, in step S47, the read acceleration value is compared with a predetermined acceleration range. When the measured value is out of the predetermined acceleration range, the it is judged that an abnormality, an application of great impact, has occurred and goes to step S48. On the other hand, when the measured acceleration value is within the predetermined acceleration range, the it is judged that the acceleration is normal and goes to step S49.

When it is detected that an acceleration becomes out of predetermined acceleration range, in step S48, an "impact flag" is turned "ON" in the memory 412 and the time when the out of the acceleration range is detected is recorded. When the flag is already ON, the first abnormality is recorded without making a new record.

Next, in step S49, the temperature value read from the sensor for outside-of-cover temperature 401 is compared with a predetermined temperature range. When the measured value is out of the predetermined temperature range, it is judged that an abnormality of outside temperature has occurred and goes to step S50. On the other hand, when the measured temperature value is within the predetermined temperature range, it is judged that the temperature outside of the cover 4A is normal and goes to step S51.

When it is detected that the temperature outside of the cover 4A becomes out of predetermined temperature range, in step S50, an "outside temperature abnormality flag" in the memory 412 is turned "ON" and the time when the out of the temperature range is detected is recorded. When the flag is already ON, the first abnormality is recorded without making a new record.

Next, in step S51, the remaining battery power (voltage) read from the sensor for remaining battery power 405 is compared with a predetermined voltage value. When the measured value is equal to or lower than the predetermined voltage value, it is judged that an abnormality of remaining battery power has occurred and goes to step S52. When the measured voltage value is over the predetermined voltage, it is judged that the remaining battery power of the battery 413 is normal and goes to step S53.

When it is detected that the remaining battery power becomes predetermined low level, in step S52, a "remaining battery power abnormality flag" in the memory 412 is turned "ON" and the time when the low battery power is detected is recorded. When the flag is already ON, the first abnormality is recorded without making a new record.

Next, in step S53, the temperature value read from the sensor for inside-of-cover temperature 402 is compared with a predetermined temperature range. When the measured value is out of the predetermined temperature range, it is judged that an abnormality of inside-of-cover temperature has occurred and goes to step S54. On the other hand, when the measured inside-of-cover temperature value is within the predetermined temperature range, it is judged that the temperature inside the cover 4A is normal and goes to step S55.

When it is detected that the temperature inside the cover 4A becomes out of predetermined temperature range, in step S54, an "inside temperature abnormality flag" in the memory 412 is turned "ON" and the time when the out of the temperature range is detected is recorded. When the flag is already ON, the first abnormality is recorded without making a new record.

Next, in step S55, a comparison is made to see whether the detected value read from the sensor for cover open and shut 406 attained a value indicating "open" (e.g., ON). When the detected value indicates "open", it is judged that an abnormality has occurred, i.e., the cover 4A opened during the transportation, and goes to step S56. On the other hand, when the detected value from the sensor for cover open and shut 406 indicates "close" (e.g., OFF), it is judged that the cover 4A is in the normal condition and goes to step S57.

When it is detected that the cover 4A opened, in step S56, a "cover-open flag" in the memory 412 is turned "ON" and the time when the opening of the cover is detected is recorded. When the flag is already ON, the first abnormality is recorded without making a new record.

In the above-described abnormality information recording steps S48, S50, S52, S54, and S56, the indicator 41 indicates occurrence of abnormality when even one of the abnormality flags is ON.

Then, in step S57, when even one of the abnormality flags of the controller 40 is ON and the currently written abnormality information indicates "normal" or abnormality of low-priority kind, the controller 30 of the transportation container for constant temperature 3 writes the kind of higher-priority abnormality information and the present time to all IC tags 10 and 20 in the transportation container for constant temperature 3. It should be noted that the priority of abnormality information is the same as that of the controller 30 of the transportation container for constant temperature 3.

On the other hand, when all abnormality flags are OFF, the indicator 41 indicates the present temperature of the carrying containers for transportation 1 or the individual carrying containers 2.

Also, the controller 40 of the carrying container writes abnormality information through the controller 30 to the IC tags 10 and 20 in the four kinds of recording modes shown below. They are previously set for each transportation container for constant temperature 3 (a switch may be provided to select the recording modes).

(D-1) No record mode: Nothing is recorded.

(D-2) All record mode: All sensor information is recorded. However, because the measured value of the sensor for acceleration 407 is obtained continuously, recording the whole information results in a huge amount of data, and so the acceleration is recorded only when an abnormality occurs. Also, because abnormality information sent from the controller 30 is written to the IC tags 10 and 20 by the controller 30, no processing and no sending to the controller 40 is performed.

(D-3) At-the-time-of-abnormality record mode: A record is made only when conditions are met in the abnormality judgements of steps S48 to S56.

The controller 40 of the carrying container 4 has the radio module 414 and communicates with the management server 5 at the control center. Then, the GPS module 416 obtains the present position of the carrying container 4.

Using the interval timer, which is not shown in the sensor controller 410, an attempt to make a circuit connection for external communication is made periodically (e.g., once in every ten minutes). When an attempt for making a connection fails, another attempt is made after a certain time period (e.g., after one minute). When the attempt fails N times (e.g., three times), the present communication processing is ended and the operation waits until the next time.

When a connection to the communication circuit has been successfully made, the abnormality information, sensor values, etc. recorded in the memory 412 and the present position of the carrying container 4 are transmitted to the management server 5.

After the transmission of information, a response signal from the recipient (management server 5) is received. When no response signal is received or when the response signal indicates "data abnormality", then the information is transmitted again.

After the transmission, the sensor values etc. recorded in the memory 412 are erased.

Through the communication above, the management server 5 accumulates, periodically (e.g. with given cycles), the conditions and present position of the carrying container for transportation 1 to the carrying container 4 being transported, allowing the sender of the medical instruments 11 and the medical facility as the consignee of the medical instruments 11 to make inquiries to the management server 5 to know the conditions and present position of the medical instruments 11 being transported.

As above, during transportation of the carrying container 4, the controller 40 performs the operations shown in FIG. 10 to monitor the conditions of the contents of the carrying container 4 (transportation containers for constant temperature 3, individual carrying containers 2, and carrying containers for transportation 1).

The time and measured values of each measurement, the digital values of identifiers, and the abnormality judgement results (flag values) are outputted from the output terminal for external data 403 of the controller 40 of the carrying container 4. Accordingly, connecting the output terminal for external data 403 to a computer carried on a vehicle, for example, makes it possible to check, at any time, the conditions of the medical instruments 11 being transported.

When the radio module 414 did not make external communication, or failed to make external communication, it may be recorded in the memory 412 as abnormality information.

Also, the controller 30 of the transportation container for constant temperature 3 may obtain a temperature gradient (and/or temperature variation) from measured temperature values obtained from the IC tags 10 and 20 and judge whether it is possible to keep the predetermined temperature range till the due time of arrival (1-1-4) written in the IC tags 10. Then, if the judgement indicates that the temperature range cannot be maintained, the possibility that the temperature may be out of the predetermined range at the time of arrival at the destination may be recorded as an abnormality, even when the present temperatures of the carrying containers for transportation 1 and individual carrying containers 2 are normal.

Particularly, the temperature retaining ability of the transportation container for constant temperature 3 depends on the amount of thermal storage of the thermal storage material 33, and the temperature retainable period varies with outside temperature. Accordingly, the temperature retainable period may be obtained on the basis of temperatures measured outside and inside the transportation container for constant temperature 3, and a warning may be displayed on the indicator 31 or 41 when the temperature retaining ability cannot be maintained until the time of arrival.

Thus, when an abnormality about temperature or the like occurs in the carrying containers for transportation 1 or individual carrying containers 2 during transportation of the medical instruments 11 including living tissues, the controller 30 of the transportation container for constant temperature 3 and the controller 40 of the carrying container 4 operate as above to cause the indicators 31 and 41 to indicate the contents of the abnormality. This makes it possible to very quickly and easily know the presence/absence of abnormality by visually checking the indicators 31 and 41 of the carrying container 4 and transportation container for constant temperature 3 before the carrying containers for transportation 1 and individual carrying containers 2 are taken out of the transportation container for constant temperature 3.

Next, a method of confirming the correctness of the carrying containers for transportation 1 will be described referring to the flowchart of FIG. 11. As shown in FIG. 7, this confirming process is conducted by using the reader/writer for IC tag 6 and the computer 60, where the computer 60 performs the operations shown in FIG. 11.

When the indicators 31 and 41 indicate no information showing abnormalities, it is ensured that the temperature and acceleration were kept normal during the transportation. A transportation container for constant temperature 3 addressed to the consignee is taken out of the carrying container 4 and an individual carrying container 2 addressed to the consignee is offered from the transportation container for constant temperature 3.

Figure 11:
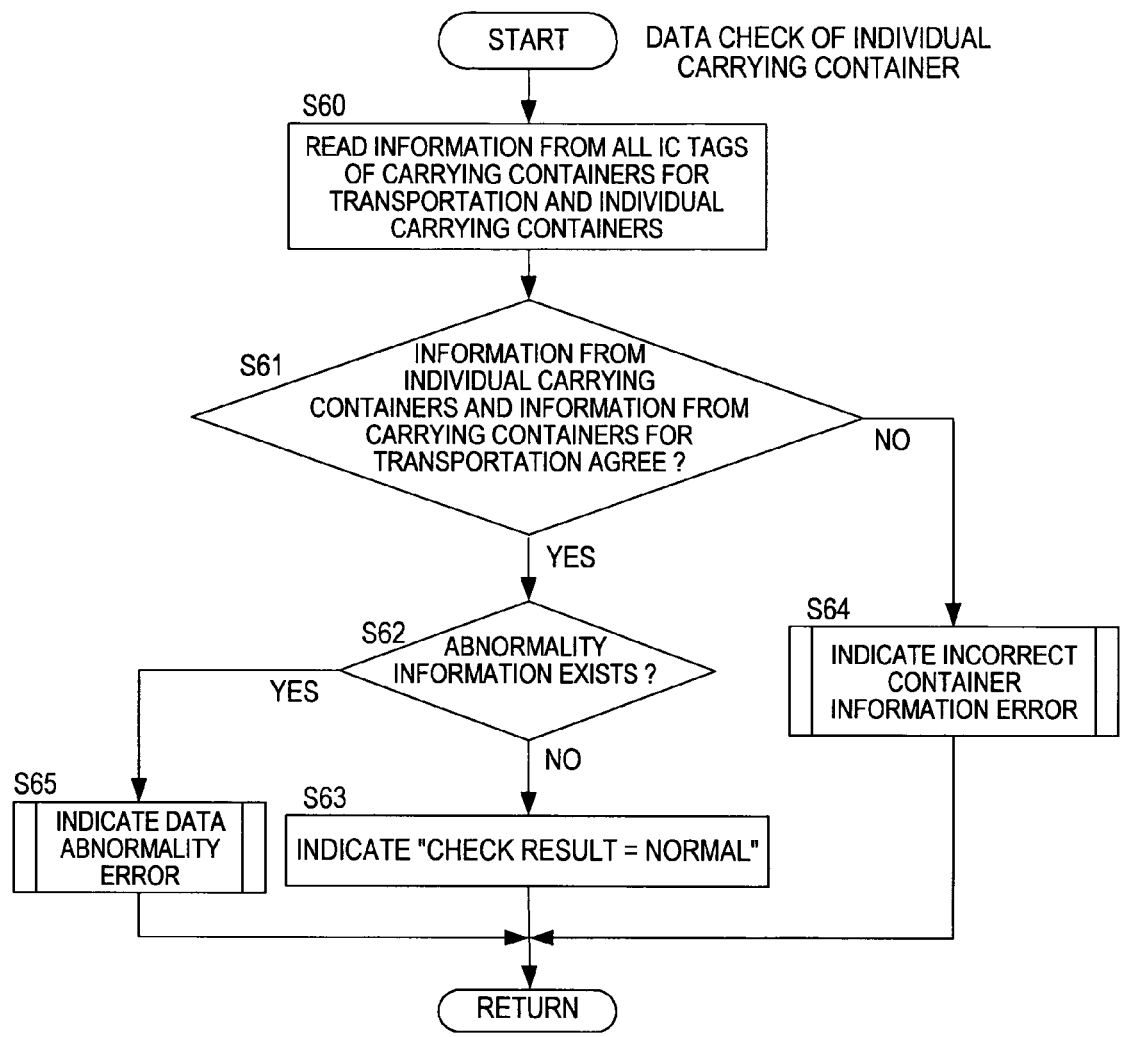
FIG. 11 is a flowchart showing a checking process performed by a computer at the destination of delivery.

The delivered individual carrying container 2 is placed on the reader/writer for IC tag 6 and then the process of FIG. 11 starts. In step S60, the identifiers of the IC tags 10 (1-2-6) of the carrying containers for transportation 1 which have been copied in step S3 and step S4 are read from the IC tag 20 of the individual carrying container 2. The identifiers are read also from the IC tags 10 of the carrying containers for transportation 1 in the individual carrying container 2.

Then, in step S61, the identifiers of the IC tags 10 of the carrying containers for transportation 1 read from the individual carrying container 2 are compared with the identifiers read from the IC tags 10 of the carrying containers for transportation 1 to judge whether they agree. When they do not agree, the processing goes to step S64 to make an indication of error showing that the identifiers of the IC tags 10 of the carrying containers for transportation 1 do not agree with the identifiers copied to the IC tag 20 of the individual carrying container 2.

When two identifiers agree, the processing goes to step S62 to check whether the IC tags 10 and 20 contain any abnormality information. When abnormality information is absent, the processing indicates in step S63 that the check results show "normal". When abnormality information is present, the processing goes to step S65 to indicate the contents of the abnormality information.

Thus, at the beginning of transportation, the identifiers of the IC tags 10 of the carrying containers for transportation 1 accommodated in the individual carrying container 2 are copied to the IC tag 20 of the individual carrying container 2, and a check is made at the destination of delivery to confirm that the identifiers copied to the IC tag 20 agree with the identifiers of the IC tags 10 of the carrying containers for transportation 1, whereby the correctness of the medical instruments 11 in the carrying containers for transportation 1 is ensured.

In the first embodiment, the labels 111 of the IC tags 10 and 20 may be temperature labels that change color depending on temperature, in which case the color of the temperature labels changes when the temperature becomes out of a predetermined range, making it possible to easily show the occurrence of a temperature abnormality.

Thus, the carrying containers for transportation 1 and individual carrying containers 2, and the passive IC tags with temperature sensors 10 and 20 attached thereto, are disposed of after use, and so the containers are kept sanitary and overwriting of identifiers is avoided, whereby reliability is ensured in sanitation aspect and correctness is ensured in information aspect. Also, because the carrying containers for transportation 1 and individual carrying containers 2, disposed of after use, are just provided with the IC tags 10 and 20, highly reliable services are offered at suppressed transportation costs.

Also, by copying the identifiers of the IC tags 10 of carrying containers for transportation 1 to the IC tag 20 of the individual carrying container 2 accommodating the carrying containers for transportation 1, and by comparing the copied identifiers and the identifiers of the IC tags 10 of the carrying containers for transportation 1, the correctness of the delivered medical instruments 11 is ensured very easily and quickly.

While the first embodiment uses a thermal storage material to maintain the temperature of the medical instruments 11, a warming device may be provided as described in the conventional example.

Also, in the first embodiment, at the beginning of transportation, the external reader/writer for IC tag 6 is used to copy the identifiers of passive IC tags with temperature sensors 10 of carrying containers for transportation 1 to the passive IC tag with temperature sensor 20 attached to the individual carrying container 2. However, the controller 30 of the transportation container for constant temperature. 3 may copy the identifiers.

Also, in the first embodiment, after transportation, the computer 60 connected to the reader/writer for IC tag 6 is used to check the identifiers of the passive IC tags with temperature sensors 10 attached to the carrying containers for transportation 1 with the identifiers of the carrying containers for transportation 1 that are stored in the passive IC tag with temperature sensor 20 attached to the individual carrying container 2. However, though not shown, a reader/writer having a checking and comparing function may be used instead.

Second Embodiment

Figure 12:
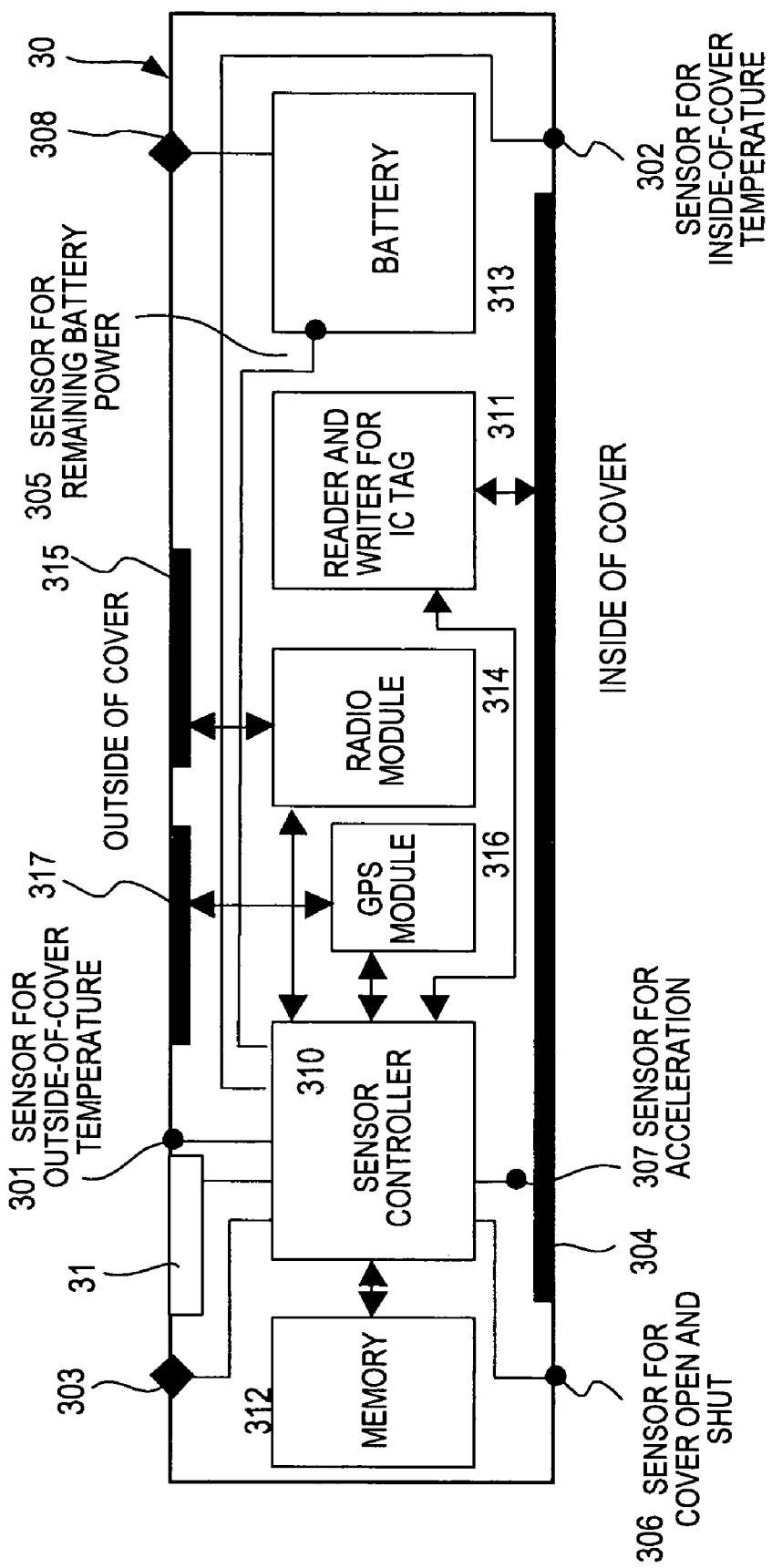
FIG. 12 is a block diagram of a controller of a constant-temperature transportation device according to a second embodiment.

FIG. 12 shows a second embodiment, where the controller 30 of the transportation container for constant temperature 3 shown in FIG. 5 includes a radio module 314, a GPS module 316, a radio terminal antenna 315, and an antenna for GPS 317. In other respects, the configuration is the same as that of the first embodiment.

In the second embodiment, the carrying containers for transportation 1 may be transported just by using the transportation container for constant temperature 3 without using the carrying container 4 of the first embodiment, and it is still possible to send the conditions of the carrying containers for transportation 1, including the present position, to the management server 5, just like the controller 40 of the carrying container 4 of the first embodiment does. In this case, in transportation of a small number of medical instruments 11 to a single destination, the removal of the need for the carrying container 4 reduces the cost.

While the embodiments above have shown examples of transportation of medical instruments 11 including living tissues, this invention is applicable to transportation of any objects that require temperature control and identification of individual objects.

Third Embodiment

Figure 13:
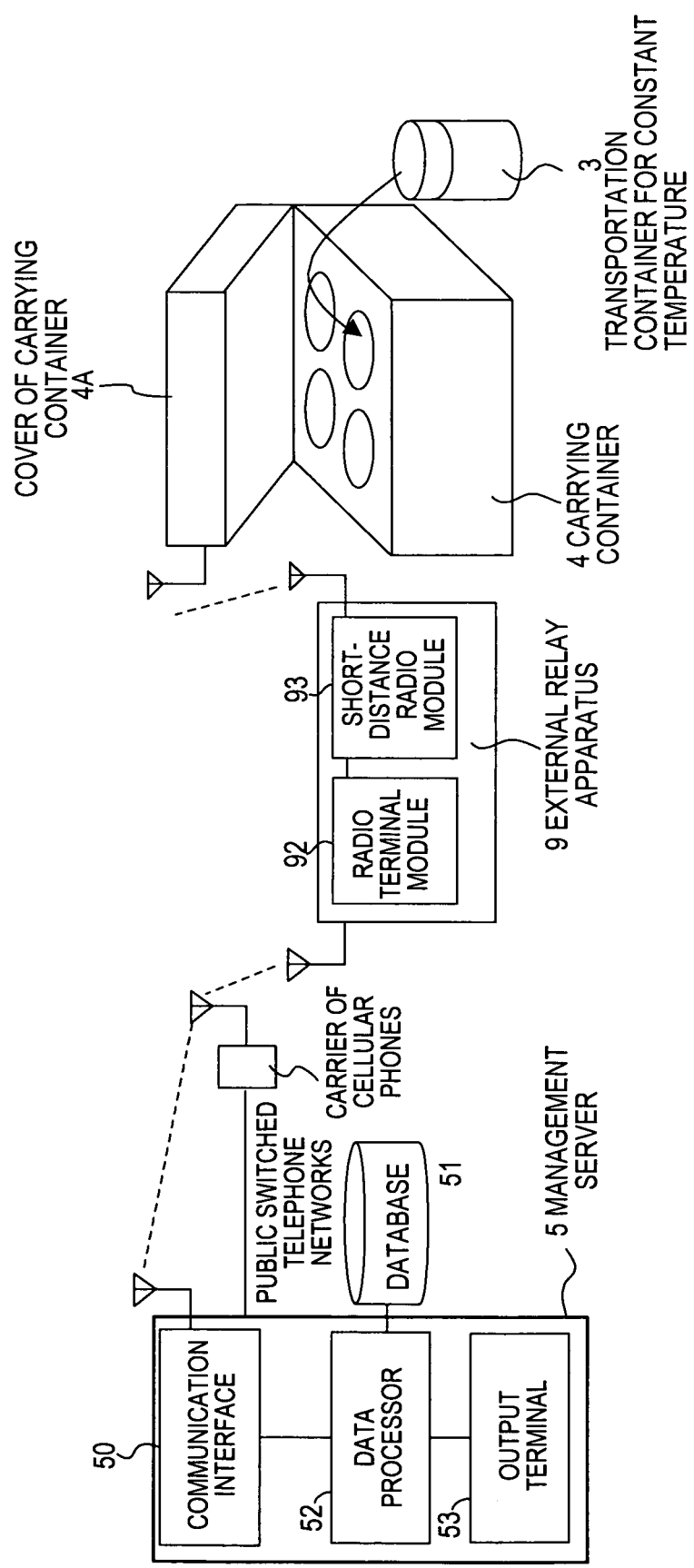
FIG. 13 is a diagram illustrating the outline of the configuration of a transportation system according to a third embodiment.

FIG. 13 shows a third embodiment, where an external relay apparatus 9 for relaying radio communication is provided between the management server 5 shown in FIG. 2 and the carrying container 4, and the radio module 414 of the controller 40 of the carrying container 4 performs short-distance radio communication. In other respects, the configuration is the same as that of the first embodiment.

In the third embodiment, the external relay apparatus 9 has a short-distance radio communication module 93 for making a connection to a short-distance radio communication network and a radio module 92 for making a connection to a cellular phone network, where the short-distance radio communication network and the cellular phone network are interswitchable.

The controller 40 of the carrying container 4 can communicate with the management server 5 by using the short-distance radio communication network to reduce consumption of the battery 413.

As has been described so far, this embodiments of this invention secures the environments of transportation and the identification of individual objects and is therefore applicable to transportation systems and transportation methods for transporting medical instruments including living tissues.

While the present invention has been described in detail and pictorially in the accompanying drawings, the present invention is not limited to such detail but covers various obvious modifications and equivalent arrangements, which fall within the purview of the appended claims.

What is claimed is:

1. A transportation device for transporting living tissues contained in a container retaining temperature, comprising:
    a first container for accommodating the living tissues;
    a second container for accommodating the first container;
    a third container provided with the temperature retaining function, for accommodating the second container;
    a first IC tag attached to the first container, the first IC tag comprising a first storage for storing a predetermined first identifier, a first temperature sensor for measuring temperature, and a radio communication module;

a second IC tag attached to the second container, the second IC tag comprising a second storage for storing an identifier same as the identifier held in the first IC tag, a second temperature sensor for measuring temperature, and a radio communication module; and a first controller provided in the third container, which communicates with the first IC tag and the second IC tag, writes and reads of information to and from the first storage and the second storage, and for obtaining the temperatures from the first temperature sensor and the second temperature sensor, wherein the first controller compares between one of the temperatures obtained from the first temperature sensor and the second temperature sensor and a predetermined temperature range, and when the obtained temperature is out of the temperature range, the first controller writes of abnormal information indicating an occurrence of a temperature abnormality to the first storage of the first IC tag and the second storage of the second IC tag.

2. The transportation device according to claim 1, wherein the third container comprises a first indicator for indicating the abnormal information controlled by the first controller when the temperature abnormality occurs, and indicates at least one of the temperatures obtained from the first temperature sensor and the second temperature sensor when no abnormality occurs.

3. The transportation device according to claim 1, wherein the first container and the second container are disposable together with the first IC tag and the second IC tag.

4. The transportation device according to claim 1, further comprising a reader/writer for reading the first identifier from the first storage of the first IC tag, and for writing the read first identifier to the second storage of the second IC tag, wherein the second storage holds a copy of the first identifier.

5. The transportation device according to claim 4, wherein the reader/writer reads the first identifier held in the first storage of the first IC tag and the copy of the first identifier held in the second storage of the second IC tag, and the transportation device further comprising a computer connected to the reader/writer judges whether or not the first identifier read from the first storage coincides with the copy of the first identifier read from the second storage.

6. The transportation device according to claim 2, wherein the third container comprises: a thermal storage material for retaining the temperatures of the first container and the second container; an inside temperature sensor for measuring a temperature inside of the third container; and an outside temperature sensor for measuring a temperature outside of the third container, and the first controller calculates a temperature retainable period based on the outside temperature, the inside temperature, and a thermal storage amount stored in the thermal storage material, and indicates a warning on the first indicator of when the temperature retainable period is expired.

7. The transportation device according to claim 1, wherein the third container comprises a communication module for connecting to a mobile communication network, and the communication module sends the temperature obtained from the first temperature sensor, the temperature obtained from the second temperature sensor and the abnormality occurrence information.

8. The transportation device according to claim 7, wherein the first controller comprises a position detecting module for detecting a present position, and the communication module, further, sends the present position information of the container.

9. The transportation device according to claim 1, further comprising:

a fourth container for accommodating the plurality of third containers; and a second controller provided in the fourth container, for communicating with the first controller of the third container, and for obtaining the temperature from the first temperature sensor, the temperature from the second temperature sensor and the abnormality occurrence information, wherein the second controller comprises a second indicator for indicating at least one of the temperatures obtained from the first temperature sensor and the second temperature sensor and the abnormality occurrence information.

10. A method of transporting living tissues contained in a container retaining temperature, comprising the steps of:

providing: a first container including a first IC tag comprising a first storage for storing a predetermined first identifier, a first temperature sensor for measuring temperature and a radio communication module; a second container including a second IC tag comprising a second storage for storing an identifier same as the identifier held in the first IC tag, a second temperature sensor for measuring temperature and a radio communication module; and a third container comprising a thermal storage material for retaining the temperatures inside the third container and a first controller;

putting the living tissues in the first container;

putting the first container in the second container;

storing a copy of the first identifier of the first IC tag in the second storage before beginning transportation of the living tissues;

putting the second container in the third container;

transporting the third container;

obtaining the temperatures from the first temperature sensor and the second temperature sensor; and writing information indicating an occurrence of a temperature abnormality to the first storage of the first IC tag and the second storage of the second IC tag when one of the temperatures obtained from the first temperature sensor and the second temperature sensor is out of a predetermined temperature range.

11. The method of transporting living tissues according to claim 10, further comprising the step of:

providing a first indicator in the third container;

indicating abnormality occurrence information when the abnormality occurs; and indicating at least one of the temperatures obtained from the first temperature sensor and the second temperature sensor when no abnormality occurs.

12. The method of transporting living tissues according to claim 10, further comprising the step of disposing of the first container without removing the first IC tag and the second container together without removing the second IC tag after the transportation.

13. The method of transporting living tissues according to claim 10, further comprising the steps of:

obtaining the first identifier from the first storage of the first IC tag after the transportation;

obtaining the copy of the first identifier held in the second storage of the second IC tag; and judging whether or not the first identifier obtained from the first storage coincides with the copy of the first identifier obtained from the second storage.

14. The living tissue transportation method according to claim 11, further comprising the steps of:

providing a thermal storage material in the third container;

measuring a temperature inside of the third container;

measuring a temperature outside of the third container;

calculating a temperature retainable period based on the outside temperature, the inside temperature, and a thermal storage amount of the thermal storage material; and indicating a warning when the temperature retainable period is expired.

15. The method of transporting living tissues according to claim 10, further comprising the step of sending the temperatures obtained from the first temperature sensor, the temperatures obtained from the second temperature sensor and the abnormality occurrence information to a management computer through a mobile communication network.

16. The method of transporting living tissues according to claim 10, further comprising the steps of:

providing a position detecting module for detecting a present position, in the first controller;

detecting a present position of the third container; and sending the present position, the temperatures obtained from the first temperature sensor, the temperatures obtained from the second temperature sensor and the abnormality occurrence information to a management computer through a mobile communication network.

17. The living tissue transportation method according to claim 10, further comprising the steps of:

providing a fourth container for accommodating the plurality of third containers, the fourth container comprising a second controller and second indicator;

putting the third container in a fourth container;

obtaining the temperature from the first temperature sensor, the temperature from the second temperature sensor and the abnormality occurrence information, by the second controller from the first controller; and indicating the temperature or the abnormality occurrence information on the second indicator.

* * * * *